(12) United States Patent
Jordan et al.

(10) Patent No.: US 9,480,280 B2
(45) Date of Patent: Nov. 1, 2016

(54) TASTE MODIFIERS

(71) Applicant: Givaudan S.A., Vernier (CH)

(72) Inventors: Jason Jordan, Cincinnati, OH (US); David C. Bom, Cincinnati, OH (US); Philip A. Christenson, Loveland, OH (US); Robert G. Eilerman, Manhasset, NY (US); Xiaogen Yang, West Chester, OH (US)

(73) Assignee: Givaudan S.A., Vernier (CH)

( * ) Notice: Subject to any disclaimer, the term of this patent is extended or adjusted under 35 U.S.C. 154(b) by 372 days.

(21) Appl. No.: 13/795,200

(22) Filed: Mar. 12, 2013

(65) Prior Publication Data

US 2013/0330457 A1 Dec. 12, 2013

Related U.S. Application Data

(60) Provisional application No. 61/658,476, filed on Jun. 12, 2012.

(51) Int. Cl.

| | | |
|---|---|---|
| *A23C 9/13* | (2006.01) | |
| *A23C 9/156* | (2006.01) | |
| *A23L 2/56* | (2006.01) | |
| *C07D 307/33* | (2006.01) | |
| *A23C 9/152* | (2006.01) | |
| *C07D 307/20* | (2006.01) | |
| *C07C 59/01* | (2006.01) | |
| *C07C 59/147* | (2006.01) | |
| *C07C 59/185* | (2006.01) | |

(52) U.S. Cl.
CPC .......... *A23L 27/2026* (2016.08); *A23C 9/1307* (2013.01); *A23C 9/1315* (2013.01); *A23C 9/156* (2013.01); *A23C 9/1528* (2013.01); *A23L 2/56* (2013.01); *A23L 27/2028* (2016.08); *A23L 27/2052* (2016.08); *A23L 27/88* (2016.08); *C07C 59/01* (2013.01); *C07C 59/147* (2013.01); *C07C 59/185* (2013.01); *C07D 307/20* (2013.01); *C07D 307/33* (2013.01)

(58) Field of Classification Search
CPC .......... A23L 1/22091; A23L 1/22671; C07D 307/20
See application file for complete search history.

(56) References Cited

U.S. PATENT DOCUMENTS

| | | | |
|---|---|---|---|
| 3,530,149 A | 9/1970 | Fiecchi | |
| 2004/0234668 A1* | 11/2004 | Matsui | A23D 9/007 426/601 |
| 2010/0062030 A1 | 3/2010 | Ley et al. | |

FOREIGN PATENT DOCUMENTS

| | | |
|---|---|---|
| EP | 0 473 842 A1 | 3/1992 |
| EP | 1 769 687 A1 | 4/2007 |
| JP | 2011-083264 A | 4/2011 |
| WO | WO 2011/145048 A1 | 11/2011 |

OTHER PUBLICATIONS

Yorimitsu, H., Wakabayashi, K., Shinokubo, H., Oshima, K. 2001. "Radical Addition of 2-Iodoalkanamide or 2-Iodialkanoic Acid to Alkenes with a Water-Soluble Radical Initiator in Aqueous Media: Facile Synthesis of γ-Lactones." Bull. Chem. Soc. Jpn. vol. 74. pp. 1963-1970.*
Rombauer, I.S., Rombauer Becker, M., Becker, E. 1997. Joy of Cooking. Scribner: New York. pp. 588,660.*
Hollnagel, A., Menzel, E.-M., Mosandl, A. 1991. "Chiral aroma compounds of sherry. II. Direct enantiomer separation of solerone and solerole." Z. Lebensm Unters Forsch. vol. 193. pp. 234-236.*
Fernandez de Simon, B., Esteruelas, E., Munoz, A.M., Cadahia, E., Sanz, M. 2009. "Volatile Compounds in Acacia, Chestnut, Cherry, Ash and Oak Woods, with a View to Their Use in Cooperage." J. Agric. Food Chem. vol. 57. pp. 3217-3227.*

(Continued)

*Primary Examiner* — Nikki H Dees
(74) *Attorney, Agent, or Firm* — Curatolo Sidoti Co., LPA; Joseph G. Curatolo; Salvatore A. Sidoti

(57) ABSTRACT

A method of modifying the taste of a consumable, comprising adding to a consumable base at least one compound of the formula I

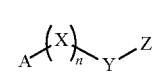

in which
(a) A is selected from the moieties

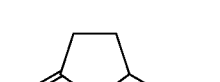

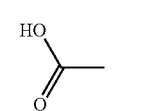

(b) n is from 0-7, such that X is absent or a linear alkylene group in which n is from 1-7; and
(c) Z is absent and Y is a moiety selected from the groups —CHO, or —CH$_2$OH; or
(d) Z is present and is a C$_{1-7}$ linear alkane, and Y is selected from —CHOH, —CO, or —COC(CH$_3$)O. The result is a consumable with enhanced mouthfeel and/or creaminess.

9 Claims, No Drawings

(56) References Cited

OTHER PUBLICATIONS

Yorimitsu, H., Wakabayashi, K., Shinokubo, H., Oshima, K. 1999. "Radical Addition of 2-Iodoalkanamide or 2-Iodialkanoic Acid to Alkenols Using a Water-Soluble Radical Initiator in Water. A Facile Synthesis of γ-Lactones." Tetrahedron Letters. vol. 40. pp. 519-522.*
Augustyn, O.P.H., Van Wyk, C.J., Muller, C.J., Kepner, R.E., Webb, A.D. 1971. "The Structure of Solerone [5-Acetyldihydro-2(3H)-furanone], a Substituted γ-lactone Involved in Wine Aroma." J. Agric. Food Chem. vol. 19. pp. 1128-1130.*
Naf, R., Jaquier, A., Boschung, A.F., Lindstrom, M. 1995. "The Sherry-lactones and Solerone. Their Identification in Dried Figs." Flavour and Fragrance Journal. vol. 10. pp. 243-247.*
Schlutt, B., Moran, N. Schieberle, Hofmann, T. 2007. Sensory-Directed Identification of Creaminess-Enhancing Volatiles and Semivolatiles in Full-Fat Cream. J. Agric. Food Chem. vol. 55. pp. 9634-9645.*
CAS Registry No. 1089324-26-4. 2008.*
Juan Chen et al., "Analysis of Aroma Components in Different Mulberry Cultivars-Honey Wines Using Gas Chromatography-Mass Spectrometry", Shipin Kexue, 2009, pp. 169-173, vol. 30, Pt 4, Zhongguo Shipin Zazhishe. Abstract Only.
Onofrio Corona, et al, "White Wine Making in the Presence of Oak Chips of Different Origin and Toasting Level", Industrie delle Bevande, 2011, pp. 24-34, vol. 40, Chiriotti Editori. Abstract Only.
R. Nishida, et al, "Male Sex Pheromone of a Giant Danaine Butterfly", Journal of Chemical Ecology, 1996, pp. 949-972, vol. 22, Issue 5, Plenum Publishers. Abstract Only.
Joachim Ruther, et al, "Pheromone Communication in Nasonia Vitripennis: Abdominal Sex Attractant Mediates Site Fidelity of Releasing Males", Journal of Chemical Ecology, 2011, pp. 161-165, vol. 37, Issue 2, Springer. Abstract Only.
Stefan Schultz, "Simple Synthesis of Enantiomers of 6-Hydroxyalkan-4-Olides by Stereoselective Hydrogenation of Methyl 4,6-Dioxoalkanoates", Chemical Communications, 1999, pp. 1239-1240, vol. 13, Royal Society of Chemistry.
Hideki Yorimitsu, et al, "Radical Addition of 2-Iodoalkanamide or 2-Iodoalkanoic Acid to Alkenols Using a Water-Soluble Radical Initiator in Water. A Facile Synthesis of γ -Lactones", Tetrahedron Letters, Jan. 15, 1999, pp. 519-522, vol. 40, Issue 3, Elsevier Ltd. Abstract Only.
H. Yorimitsu, et al, "Radical Addition of 2-Iodoalkanamide or 2-Iodoalkanoic Acid to Alkenes With a Water-Soluble Radical Initiator in Aqueous Media: Facile Synthesis of γ-Lactones", Bulletin of the Chemical Society of Japan, 2001, pp. 1963-1970, vol. 74, Issue 10. Abstract Only.
Birgit Schlutt, et al "Sensory-Directed Identification of Creaminess-Enhancing Volatiles and Semivolatiles in Full-Fat Cream", Journal of Agricultural and Food Chemistry, Oct. 13, 2007, pp. 9634-9645, vol. 55, Issue 23, American Chemical Society. Abstract Only.
GB Search Report No. 1215740.0, mailed Dec. 20, 2012.
PCT/EP2013/062007—International Search Report, mailed Dec. 5, 2013.
PCT/EP2013/062007—International Preliminary Report on Patentability, issued Dec. 16, 2014.
Muller, C J., et al., "Identification of 2 Isomers of 4 5 Di Hydroxy Hexanoic-Acid Gamma Lactone in Californian and Spanish Flor Sherries", Journal of Agriculture and Food Chemistry, 1969, pp. 1373-1376, vol. 17, No. 6.
Nobuhara, A., "Synthesis of Unsaturated Lactones, Part IV, Flavourous Nature of Some Aliphatic Γ-Lactones", Agricultural and Biological Chemistry, 1970, pp. 1745-1747, vol. 34, No. 11.

* cited by examiner

TASTE MODIFIERS

The present application claims the benefit of the filing date, pursuant to 35 U.S.C. §119 (e), of U.S. Provisional Application for Patent Ser. No. 61/658,476, filed Jun. 12, 2012, incorporated herein by reference.

This description relates to the modification of taste, and to compounds for modifying taste.

Compounds for modifying the taste of consumables such as foodstuffs, beverages, confectionery and the like are widely used. They do not themselves add flavour to the consumable, but they provide desirable ancillary benefits, such as enhanced mouthfeel and creaminess, or masking undesirable characteristics of other ingredients, such as the bitter aftertaste associated with some sweeteners used in place of sugar in dietary products.

There have been investigations of the sources of creaminess in full-fat cream, for example, by Schlutt et al in *J. Agr. Food. Chem.* 2007, 55, 9634-9645. A range of compounds, including a number of lactones, was tested, and it was found that only δ-tetradecalactone was able to enhance the retronasal cream flavour in a product, other lactones merely influencing the melting behaviour of cream in the mouth. Japanese publication 2011-083264 additionally found that certain δ-lactones could contribute to creamy sensation.

There is now provided a class of compounds that provides such desirable effects. This disclosure provides a method of modifying the taste of a consumable, comprising adding to a consumable base at least one compound of the formula 1

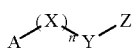

I in which
(a) A is selected from the moieties

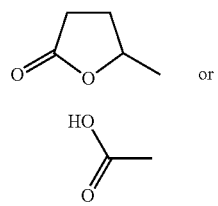

(i) or (ii)

(b) n is from 0-7, such that X is absent or a linear alkylene group in which n is from 1-7; and
(c) Z is absent and Y is a moiety selected from the groups —CHO, or —CH$_2$OH; or
(d) Z is present and is a C$_{1-7}$ linear alkane, and Y is selected from —CHOH, —CO, or —COC(CH$_3$)O.

Particular examples of compounds am 8-hydroxydecanoic acid and 9-hydroxydecanoic acid. Although these compounds are known, their use in flavor applications is not.

Some of the taste modifiers are novel compounds. There is therefore also provided a compound of the formula II,

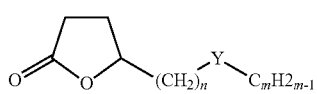

II in which the values of n, m and Y are selected according to the following table:

| n | Y | m |
|---|---|---|
| 1 | CO | 2, 3, 5, 6 |
| 1 | CHOH | 2, 3 |
| 1 | COC(CH$_3$)O | 4 |
| 3 | CO or CHOH | 1, 2, 3 |
| 3 | COC(CH$_3$)O | 2 |
| 4 | CO | 2, 3 |
| 4 | CHOH | 1, 2, 3 |
| 4 | COC(CH$_3$)O | 1 |
| 5 | CO | 1, 2 |
| 5 | CHOH | 1 |
| 5 | CH$_2$OH | — |
| 5 | CHO | — |
| 6 | CO | 1 |
| 6 | CH$_2$OH | — |
| 6 | CHO | — |
| 7 | CHO | — |

Particular examples of these novel compounds are 8-hydroxy gamma decalactone and 9-hydroxy gamma decalactone.

Preparation of Materials

The synthesis of the hydroxy-γ-lactones 3 may be carried out in one step from the appropriate hydroxyolefin 2 using a radical-mediated atom transfer cyclization approach, scheme 3 (Yorimitsu, Hideki; Wakabayashi, Katsuyu; Shinokubo, Hiroshi and Oshima, Koichiro, Bulletin of the Chemical Society of Japan (2001), 74(10), 1963-1970). Alternatively, if the desired hydroxylolefin 2 is not commercially available then it can be prepared in two steps from the commercial hydroxyolefin by oxidation to the aldehyde using PDC. Dess-Martin reagent or another aldehyde selective oxidant familiar to those skilled in the art. One skilled in the art will recognize that there are numerous ways that one might prepare the hydroxyolefin starting materials. One important point is that if n=2, then the cyclization of the hydroxyl may occur providing carboxytetrahydrofurans as byproducts (Yorimitsu, Hideki; Wakabayashi, Katsuyu; Shinokubo, Hiroshi; Oshima, Koichiro, Tetrahedron Letters (1999), 40(3), 519-522).

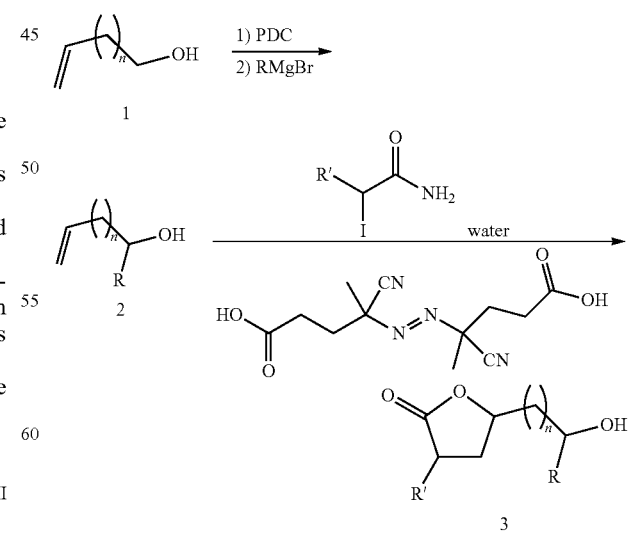

The compounds hereinabove described may be added to consumable bases. A consumable base is the totality of all the ingredients of consumable, except for the compound hereinabove defined. These ingredients will depend on the nature of the consumable and may be selected from any of those known to and used by the art, in art-recognised quantities.

These include, but are not limited to, anti-caking agents, anti-foaming agents, anti-oxidants, binders, colourants, diluents, disintegrants, emulsifiers, encapsulating agents or formulations, enzymes, fats, flavour-enhancers flavouring agents, gums, lubricants, polysaccharides, preservatives, proteins, solubilisers, solvents, stabilisers, sugar-derivatives, surfactants, sweetening agents, vitamins, waxes, and the like. Solvents which may be used are known to those skilled in the art and include e.g. ethanol, ethylene glycol, propylene glycol, glycerine and triacetin. Encapsulants and gums include maltodextrin, gum arabic, alginates, gelatine, modified starch, and polysaccharides. Examples of additives, excipients, carriers, diluents or solvents for flavour or fragrance compounds may be found e.g. in "Perfume and Flavour Materials of Natural Origin", S. Arctander, Ed., Elizabeth, N.J. 1960; in "Perfume and Flavour Chemicals", S. Arctander, Ed., Vol. I & II. Allured Publishing Corporation, Carol Stream, USA, 1994; in "Flavourings", E. Ziegler and H. Ziegler (ed.). Wiley-VCH Weinheim, 1998, ad "CTFA Cosmetic Ingredient Handbook", J. M. Nikitakis (ed.). 1st ed. The Cosmetic, Toiletry and Fragrance Association, Inc., Washington, 1988.

The proportion of the compound hereinabove described (more than one may be used) used in a consumable will vary according to the nature of the consumable and the nature and strength of the effect desired by the flavorist. However, typical non-limiting proportions are from 0.3-20 ppm when A is (i) and from 0.5-25 ppm when A is (ii).

The compounds may be used in any kind of consumable. Non-limiting examples of such consumables include:

wet/liquid soups regardless of concentration or container, including frozen soups. For the purpose of this definition soup(s) means a food prepared from meat, poultry, fish, vegetables, grains, fruit and other ingredients, cooked in a liquid which may include visible pieces of some or all of these ingredients. It may be clear (as a broth) or thick (as a chowder), smooth, pureed or chunky, ready-to-serve, semi-condensed or condensed and may be served hot or cold, as a first course or as the main course of a meal or as a between meal snack (sipped like a beverage). Soup may be used as an ingredient for preparing other meal components and may range from broths (consommé) to sauces (cream or cheese-based soups);

dehydrated and culinary foods, including cooking aid products such as: powders, granules, pastes, concentrated liquid products, including concentrated bouillon, bouillon and bouillon like products in pressed cubes, tablets or powder or granulated form, which are sold separately as a finished product or as a ingredient within a product, sauces and recipe mixes (regardless of technology);

meal solutions products such as: dehydrated and freeze dried soups, including dehydrated soup mixes, dehydrated instant soups, dehydrated ready-to-cook soups, dehydrated or ambient preparations of ready-made dishes, meals and single serve entrees including pasta, potato and rice dishes;

meal embellishment products such as: condiments, marinades, salad dressings, salad toppings, dips, breading, better mixes, shelf stable spreads, barbecue sauces, liquid recipe mixes, concentrates sauces or sauce mixes, including recipe mixes for salad, sold as a finished product or as an ingredient within a product, whether dehydrated, liquid or frozen;

beverages, including beverage mixes and concentrates, including but not limited to, alcoholic and non-alcoholic ready to drink and dry powdered beverages, carbonated and non-carbonated beverages e.g. sodas, fruit or vegetable juices, alcoholic and non-alcoholic beverages, confectionery products, e.g. cakes, cookies, pies, candies, chewing gums, gelatins, ice creams, sorbets, puddings, jams, jellies, salad dressings, and other condiments, cereal, and other breakfast foods, caned fruits and fruit sauces and the like;

milk, cheese, yoghurt and other dairy products.

The addition of the compounds hereinabove described confers desirable effects on the consumables, such as increased creamyness/mouthfeel in a yogurt or low-fat milk product, and the masking of bitter after-tastes in consumables containing ingredients that are bitter or that have bitter after-tastes. Particular examples are materials such as whey protein frequently found in dairy applications, and high-intensity sweeteners with known bitter lingering such as rebaudioside A, Aspartame™, Acesulfame K™ and scralose, frequently used in beverages and low sugar dietary/health products. The concentrations for use in these uses may vary over a wide range, depending on the nature of the consumable and the desired end-result, but typical figures are shown in the following table:

| moiety | Creaminess/mouthfeel | masking |
| --- | --- | --- |
| (i) | 3-20 ppm | 0.3-15 ppm |
| (ii) | 2-25 ppm | 0.5-15 ppm |

(The moieties refer to those of the formulae above. The ppm are with reference to the entire consumable.)

The disclosure is further described with reference to the following non-limiting examples.

EXAMPLE 1

5-(5-hydroxyhexyl)dihydrofuran-2(3H)-one

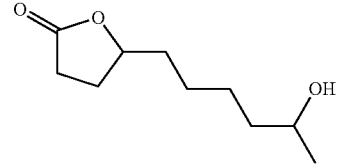

a) hept-6-enal<sup>a</sup>

Celite (26.9, 100 mmol) and pyridinium chlorochromate (28.3 g, 131 mmol) were placed in a 500 ml round bottom flask equipped with a stir bar and Dichloromethane (225 ml) was added. This orange slurry was stirred for five minutes at 22° C. Next, hept-6-en-1-ol (10 g, 88 mmol) was added and the contents were stirred at 22° C. After 2.5 hours, the reaction was determined to be complete by TLC (70:30 hexane:EtOAc) using potassium permanganate stain to visualize the spots. The reaction was filtered through a pad of silica gel using 9.1 pentane:MTBE (500 ml). The eluant was distilled off at atmospheric pressure followed by further evaporation by rotavap, with the water bath at 22° C. and the vacuum at 180 mbar. This provided hept-6-enal (9.8 g, 100%) as a clear oil, which was used without further purification. $^1$H NMR (300 MHz, CDCl$_3$, ppm) 1.38-1.49 (m, 2H), 1.60-1.70 (m, 2H), 2.04-2.12 (m, 2H), 2.44 (ddd, J$_1$=7 Hz, J$_2$=2 Hz, 2H), 4.94-5.05 (m, 2H), 5.72-5.86 (m, 1H), 9.77 (t, J=2 Hz, 1H); $^{13}$C NMR (75 MHz, CDCl$_3$, ppm)

21.7, 28.5, 33.6, 43.9, 115.0, 138.4, 202.7; GC/MS calculated for $C_7H_{12}O$ 112, observed (M−1) 111.

*Rosillo, Marta; Armaiz Eduardo; Abdi, Delbrin; Blanco-Urgoiti, Jaime; Dominguez, Gema; Perez-Castells, Javier. European Journal of Organic Chemistry (2008), (23), 3917-3927.

b) oct-7-en-2-ol

Hept-6-enal (9.51 g, 85 mmol) from step a) above was dissolved in Diethyl ether (200 ml) and cooled to 5° C. Next, methylmagnesium bromide (26.5 ml, 85 mmol) was added dropwise maintaining an internal reaction temperature between 8° and 9.5° C. After the addition was complete, the reaction stirred for 1.5 hours at 5° C. A TLC using 80:20 hexane:EtOAc staining with potassium permanganate was made against the starting material. The starting material had been consumed and a new, more polar spot was observed. The reaction was carefully quenched with saturated ammonium chloride (30 ml) producing a white suspension. The contents were transferred to a 1 L separatory funnel and diluted with MTBE (300 ml) and water (100 ml). The layers were separated and the aqueous was extracted with MTBE (75 ml). The organic layers were combined, dried ($Na_2SO_4$), filtered and concentrated. This product was isolated as a clear oil and used without further purification. $^1$H NMR (300 MHz, $CDCl_3$, ppm) 1.18 (d, J=6 Hz), 1.28-1.50 (m, 6H), 1.75-1.88 (br s, 1H), 2.00-2.12 (m, 2H), 3.73-3.82 (m, 1H), 4.92-5.03 (m, 2H), 5.74-5.87 (m, 1H); $^{13}$C NMR (75 MHz, $CDCl_3$, ppm) 23.6, 25.4, 29.0, 33.8, 39.3, 68.1. 114.5, 139.0; GC/MS calculated for $C_8H_{16}O$ 128, observed (M−1) 127.

c) 5-(5-hydroxyhexyl)dihydrofuran-2(3H)-one

Oct-7-en-2-ol (2 g, 15.60 mmol) was added to a 4 dram vial followed by 2-iodoacetamide (0.962 g, 5.20 mmol). Water (0.52 ml) and (E)-4,4'-(diazene-1,2-diyl)bis(4-cyanopentanoic acid) (0.729 g, 2.60 mmol). The contents were sparged with argon for five minutes and then capped under Argon and heated to 75° C. in the dark, overnight. The next day, the contents were transferred to saturated $NaHCO_3$ (25 ml) and extracted with EtOAc (2×50 ml). The organic layer was dried ($Na_2SO_4$), filtered and concentrated. The crude was purified on $SiO_2$ using a gradient of 100% hexane to 100% EtOAc staining with $KMnO_4$ to visualize the spots. The semi-pure oil derived from the first chromatography was taken up in a small amount of DCM and rechromatographed using a 408 high resolution (silicycle) $SiO_2$ column ad gradient of 100% hexane to 100% EtOAc provided the above titled product (194 mg, 20%) as a mixture of diastereomers. $^1$H NMR (300 MHz, $CDCl_3$, ppm) 1.19 (d, J=6 Hz, 3H), 1.35-1.50 (m, 7H), 1.55-1.93 (m, 3H), 2.26-2.38 (m, 1H), 2.50-2.56 (m, 2H), 3.74-3.84 (br m, 1H), 4.44-4.54 (m, 1H); $^{13}$C NMR (75 MHz, $CDCl_3$, ppm) 23.8, 25.5, 25.6, 25.7, 28.2, 29.0, 35.7, 35.8, 39.2, 68.1, 81.1, 177.4; GC/MS calculated for $C_{10}H_{18}O_3$ 186, observed (M−2) 184.

EXAMPLE 2

5-(4-hydroxyhexyl)dihydrofuran-2(3H)-one

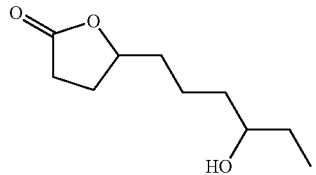

a) hex-5-enal

Celite (26.9 g, 100 mmol) and pyridinium chlorochromate (32.3 g, 150 mmol) ere placed in a 500 ml round bottom flask equipped with a stir bar and dichloromethane (225 ml). The orange slurry was stirred for five minutes at room temperature. Next, hex-5-en-1-ol (10 g, 100 mmol) was added over two minutes and the contents were stirred at room temperature for 2.5 hours. TLC (70:30 hexane:EtOAc), using potassium permanganate stain to visualize the spots, indicated a complete reaction. The reaction was filtered through a pod of silica gel using 9:1 pentane:MTBE (500 ml). The eluant was distilled off at atmospheric pressure. The contents were placed on the rotavap, with the water bath at room temperature and the vacuum at 180 mbar. This provided the desired product as a clear oil (5.89 g, 60.1%) which was used without further purification. $^1$H NMR (300 MHz, $CDCl_3$, ppm) 1.64-1.80 (m, 2H), 2.04-2.10 (m, 2H), 2.45 (dt, $J_1$=7 Hz, $J_2$=2 Hz, 2H), 4.94-5.07 (m, 2H), 5.70-5.84 (m, 1H), 9.77 (t, J=2 Hz); $^{13}$C NMR (75 MHz, $CDCl_3$, ppm) 21.3, 33.1, 43.2, 115.7, 137.7, 202.6; GC/MS calculated for $C_6H_{10}O$ 98, observed 98.

b) oct-7-en-3-ol

Hex-5-enal (5.89 g, 60.0 mmol) was added to a 500 ml 3-neck flask and dissolved in dry diethyl ether (200 ml). This solution was cooled using an ice bath. Monitoring the reaction temperature and maintaining it between 7° and 10° C. a solution of ethylmagnesium bromide (60.0 ml, 60.0 mmol) was added such that the reaction temperature never rose above 10° C. After the addition was complete, the reaction stirred for 1.5 hours at 5° C. A TLC (80:20 hexane:EtOAc visualizing spots with potassium permanganate stain), which indicated that the starting material had been consumed and a new, more polar spot had been generated. The reaction was carefully quenched with saturated ammonium chloride (30 ml) producing a white suspension. The contents were transferred to a 1 L separatory funnel and diluted with MTBE (300 ml) and water (100 ml). The layers were separated and the aqueous was extracted with MTBE (75 ml). The organic layers were combined, dried ($Na_2SO_4$), filtered and concentrated. This product was isolated as a clear oil and used without further purification. $^1$H NMR (300 MHz, $CDCl_3$, ppm) 0.94 (t, J=7 Hz, 3H), 1.35-1.61 (m, 6H), 1.70-1.91 (m, 1H), 2.01-2.12 (m, 2H), 3.49-3.54 (m, 1H), 4.92-5.04 (m, 2H), 5.74-5.88 (m, 1H); $^{13}$C NMR (75 MHz, $CDCl_3$, ppm) 10.0, 25.1, 30.3, 33.9, 36.5, 73.2, 114.6, 138.9; GC/MS calculated for $C_8H_{16}O$ 128, observed (M−H) 127.

c) 5-(4-hydroxyhexyl)dihydrofuran-2(3H)-one

Oct-7-en-3-ol (2 g, 15.60 mmol) was added to a 4 dram vial followed by 2-iodoacetamide (0.962 g, 5.20 mmol). Water (0.52 ml) and (E)-4,4'-(diazene-1,2-diyl)bis(4-cyanopentanoic acid) (0.729 g, 2.60 mmol). The contents were sparged with argon for five minutes and then capped under Argon and heated to 75° C. in the dark, overnight. The next day, the contents were transferred to saturated $NaHCO_3$ (25 ml), and extracted with EtOAc (2×50 ml). The organic layer was dried ($Na_2SO_4$), filtered and concentrated. The crude was purified on $SiO_2$ using a gradient of 100% hexane to 100% EtOAc staining with $KMnO_4$ to visualize the spots. Concentration of the product containing fractions gave an oil, which was taken up in a small amount of DCM and rechromatographed using a 40 g high resolution (silicycle) $SiO_2$ column and a gradient of 100% hexane to 100% EtOAc. Careful TLC (75%:25% EtOAc:hexane) elating each plate two times and staining with $KMnO_4$ allowed the separation of the desired product from a less polar byproduct. $^1$H NMR (300 MHz, $CDCl_3$, ppm) 0.94 (t, J=7 Hz, 3H), 1.36-1.52 (m, 7H), 1.55-1.93 (m, 3H), 2.28-2.39 (m, 1H), 2.51-2.56 (m, 2H), 3.51-3.55 (m, 1H), 4.47-4.53 (m, 1H); $^{13}$C NMR (75 MHz, CDCl$_3$, ppm) 10.0, 21.6, 21.8, 28.1, 28.2, 29.0, 30.4, 35.7, 35.8, 36.6, 36.7, 73.1, 73.2, 81.06, 81.1, 177.4; GC/MS calculated for C$_{10}$H$_{18}$O$_3$ 186, observed (M−2) 184.

EXAMPLE 3

5-(2-hydroxyheptyl)dihydrofuran-2(3H)-one

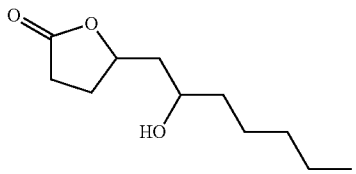

Non-1-en-4-ol (10 g, 70.3 mmol) was added to a 4 dram vial followed by Water (2.34 ml). 2-iodoacetamide (4.33 g, 23.43 mmol) and (E)-4,4'-(diazene-1,2-diyl)bis(4-cyanopentanoic acid) (3.28 g, 11.72 mmol). The mixture was sparged with argon for 5 minutes and then capped under argon and heated to 75° C. overnight in the dark. The next morning the reaction was poured into saturated NaHCO$_3$ (80 ml) and extracted with ethyl acetate (2×200 ml). The ethyl acetate layer was dried (Na$_2$SO$_4$) and then evaporated providing a dark orange oil. A TLC (50:50 hexane:EtOAc visualization with potassium permanganate stain) showed the unreacted nonenol (Rf~0.8-0.9) along with a new spot lower on the plate (Rf~0.3-0.4). The product was purified by chromatography using a gradient or 100% hexane to 40:60 hexane:EtOAc. Isolation of the product containing fractions provided a clear oil (3.48 g, 74.1%), which contained a mixture of diasteromers. $^1$H NMR (300 MHz, CDCl$_3$, ppm) 0.89 (t, J=7 Hz, 3H), 1.25-1.40 (m, 5H), 1.41-1.55 (m, 3H), 1.62-1.98 (m, 3H), 2.10-2.22 (br s, 1H), 2.31-2.45 (m, 1H), 2.51-2.55 (m, 2H), 3.76-3.91 (m, 1H), 4.65-4.85 (m, 1H); $^{13}$C NMR (75 MHz, CDCl$_3$, ppm) 14.2, 22.8, 25.3, 28.5, 28.67, 28.7, 29.1, 31.9, 37.7, 38.2, 42.8, 43.3, 68.6, 69.5, 78.4, 79.7, 177.1, 177.4; GC/MS calculated for C$_{11}$H$_{20}$O$_3$ 200, observed (M−1) 199.

EXAMPLE 4

5-(1-hydroxyhexyl)dihydrofuran-2(3H)-one

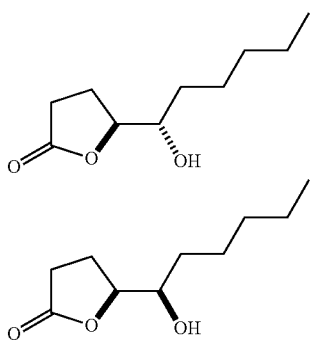

a) 5-(1-hydroxyhexyl)furan-2(5H)-one

Dichloromethane (64 ml) and hexanal (1.567 ml, 12.80 mmol) was added to a 250 ml round bottom flask and cooled to −78° C. Next, (furan-2-yloxy)trimethylsilane (2.105 ml, 12.80 mmol) and hexanal (1.567 ml, 12.80 mmol) were added followed by triethylsilyl trifluoromethanesulfonate (0.579 ml, 2.56 mmol). The contents were stirred at −78° C. for 2 hours. After 2 hours. 2 M HCl was added (10 ml) and the consents were warmed to room temperature, washed with brine (2×50 ml) and dried (MgSO$_4$). The solvent was evaporated and the residue was purified by flash chromatography on SiO$_2$ using a gradient of 100% hexane to 50:50 hexane:EtOAc providing the desired product (1.37 g, 58.1%) as a clew oil. GC/MS calculated for C$_{10}$H$_{16}$O$_3$ 184, observed 184.

b) 5-(-1-hydroxyhexyl)dihydrofuran-2(3H)-one 5-(1-Hydroxyhexyl)furan-2(5H)one (1.37 g, 7.44 mmol) was dissolved in ethyl acetate (20 ml) and treated with Pd/C 10% (0.137 g). The contents were pumped and purged 4-5 times with Ar. Finally, a balloon of hydrogen was added and the pump purge cycle was repeated with hydrogen. The reaction was stirred overnight. The next day, the reaction was filtered through celite, washing well with EtOAc and the solvent was concentrated. The product was purified by flash chromatography on SiO$_2$ using a gradient of 100% hexane to 50:50 hexane/EtOAc. This provided the desired product (1.32 g, 95%), a clear oil, as an 8:2 mixture of threo (major) and crythro (minor). $^1$H NMR (300 MHz, CDCl$_3$, ppm) 0.90 (t, J=7 Hz, 3H), 1.23-1.38 (m, 5H), 1.48-1.61 (m, 3H), 2.10-2.31 (m, 2H), 2.46-2.67 (m, 3H), 3.51-3.61 (br m, 0.8H), 3.88-3.95 (br m, 0.2H), 4.40-4.47 (m, 1H); $^{13}$C NMR (75 MHz, CDCl$_3$, ppm) 14.1, 21.2, 22.6, 24.2, 25.3, 25.4, 2.8, 28.9, 31.8, 31.83, 32.1, 33.0, 71.5, 73.6, 83.1, 83.2, 177.7, 177.9; GC/MS calculated for C$_{10}$H$_{18}$O$_3$ 186, observed 186.

EXAMPLE 5

9-oxodecanoic Acid

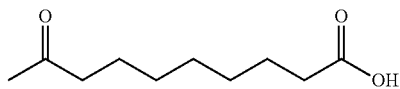

a) Diethyl 2-acetylnonanedioate

Ethyl 7-bromoheptanoate (10 g, 42.2 mmol) was dissolved in Acetone (56 ml) and treated with ethyl 3-oxobutanoate (5.49 g, 42.2 mmol) and potassium carbonate (23.31 g, 169 mmol). The resulting suspension was stirred vigorously and heated to reflux overnight. The next day the reaction was cooled and the solids were removed by suction filtration. The solvent was concentrated and the residue was taken up in dichloromethane, filtered and chromatographed on silica gel using a gradient of 100% hexane to 80:20 hexane:EtOAc. TLC, staining with KMnO$_4$, and pooling of the product fractions provided the desired product as a clear oil (7.45 g, 61.7%). GC/MS calculated for C$_{15}$H$_{26}$O$_5$ 286, observed 286.

b) 9-oxodecanoic Acid

Diethyl 2-acetylnonanedionate (4.14 g, 14.46 mmol) was treated with sodium hydroxide (30 ml, 120 mmol) (4 M) and Ethanol (30 ml). This was refluxed for 5 hours and then cooled to room temperature. The reaction was partially concentrated on the rotavap to remove some ethanol. Next, it was transferred to a 250 ml separatory funnel and washed with MTBE (2×75 ml). The aqueous layer was cooled to 0° C. and made acidic (pH~1) using concentrated HCl. Next, the acidified solution was extracted with dichloromethane, dried (Na$_2$SO$_4$) filtered and concentrated providing an off-white solid (1.69 g, 63%). $^1$H NMR (300 MHz, CDCl$_3$, ppm) 1.25-1.38 (br m, 6H), 1.51-1.68 (m, 4H), 2.13 (s, 3H), 2.34 (t, J=7 Hz, 2H), 2.42 (t, J=7 Hz, 2H), 10.90 (br s, 1H); $^{13}$C NMR (75 MHz, CDCl$_3$, ppm) 23.9, 24.8, 29.0, 29.1, 29.2, 30.0, 34.1, 43.9, 179.7, 209.5;

EXAMPLE 6

9-hydroxydecanoic Acid

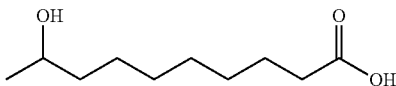

a) methyl 9-oxodecanoate 9-oxodecanoic acid, from example 5 above, (0.5 g, 2.68 mmol) was added to a 50 ml round bottom flask followed by Methanol (11 ml) and amberlyst 15 (0.43 g, 2.68 mmol). The contents were stirred at room temperature following the reaction by TLC. After 24 hours, the amberlyst was removed by filtration through filter paper and the methanol was evaporated. The product was chromatographed on silica gel using a gradient of 100% hexane to 50:50 hexane:EtOAc. The product containing fractions were combined and evaporated providing the desired product, (0.43 g, 80%), as a clear oil. GC/MS calculated for $C_{11}H_{20}O_3$ 200, observed 200.

b) methyl 9-hydroxydecanoate

Methyl 9-oxodecanoate (0.4305 g, 2.150 mmol) was dissolved in Methanol (10 ml) and cooled to 0° C. Next, sodium borohydride (0.089 g, 2.365 mmol) was added and the reaction was warmed to room temperature for 1 hour. After an hour, the starting material had been consumed based on TLC analysis (70:30 hexane:EtOAc) staining KMnO$_4$. The reaction was cooled to 0° C. and quenched with saturated NH$_4$Cl. A white precipitate formed, which was removed by filtration and washing with MeOH. The filtrate was evaporated, diluted with water and extracted with EtOAc. The EtOAc layer was dried (N$_2$SO$_4$), filtered and concentrated providing a clear oil. The product was dissolved in a small amount of DCM and chromatographed on a 40 g SiO$_2$ column using a gradient of 100% hexane to 50.50 hexane:EtOAc. The fractions were analyzed by TLC 70:30 hexane:EtOAc and product containing fractions were combined and concentrated providing methyl 9-hydroxydecanoate (0.31 g, 71%) as a clear oil. $^1$H NMR (300 MHz, CDCl$_3$, ppm) 1.16 (d, J=6 Hz, 3H), 1.23-1.42 (m, 11H), 1.57-1.63 (m, 2H), 2.22 (t, J=7 Hz, 2H), 3.64 (s, 3H), 3.73-3.80 (m, 1H); $^{13}$C NMR (75 MHz, CDCl$_3$, ppm) 23.7, 25.1, 25.9, 29.3, 29.4, 29.6, 34.3, 39.5, 51.6, 68.3, 174.5; GC/MS calculated for $C_{11}H_{22}O_3$ 202, observed (M-CH$_3$) 187.

c) 9-hydroxydecanoic Acid

Methyl 9-hydroxydecanoate (0.3108 g, 1.536 mmol) was dissolved in THF (5 ml) and methanol (5 ml) and cooled to 0° C. Next, lithium hydroxide (0.922 ml, 1.844 mmol) was added and the reaction was warmed to room temperature. The progress was monitored by TLC (70:30 hexane:EtOAc) staining with KMnO$_4$. After 3 hours, starting material still remained so an additional 0.9 ml of 2M LiOH was added and stirring was continued. After 6 hours, a TLC showed that the starting material had largely been consumed. The reaction was concentrated on the rotavap to remove the methanol and THF. The residue was diluted with 1M KOH (15 ml) and washed with MTBE (2×30 ml). The aqueous layer was cooled to 0° C. and adjusted to pH~1 by dropwise addition of concentrated HCl. The product was extracted using ethyl acetate (2×50 ml). The ethyl acetate layer was dried (Na$_2$SO$_4$), filtered and concentrated providing a clear oil. The oil was placed on the vacuum pump overnight at 50° C. providing the 9-hydroxydecanoic acid (0.25 g, 86%) as a clear oil. $^1$H NMR (300 MHz, CDCl$_3$, ppm) 1.19 (d, J=6H, 3H), 1.25-1.45 (m, 11H), 1.5-1.66 (m, 2H), 2.35 (t, J=7 Hz, 2H), 3.76-3.83 (m, 1H); $^{13}$C NMR (75 MHz, CDCl$_3$, ppm) 23.7, 24.8, 25.8, 29.1, 29.3, 29.6, 34.1, 39.5, 68.4, 179.1.

EXAMPLE 7

8-oxodecanoic Acid

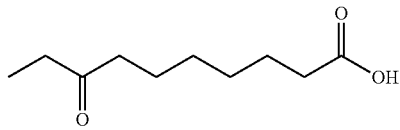

a) 8-ethyl 1-methyl 2-propionyloctanedioate

Ethyl 6-bromohexanoate (10 g, 44.8 mmol) was dissolved in Acetone (56 ml) and treated with methyl 3-oxopentanoate (5.63 ml, 44.8 mmol) and potassium carbonate (24.78 g, 179 mmol). The contents were heated to reflux overnight with vigorous stirring. The next day the salts were filtered off and the solvent was evaporated. The solvent was concentrated and the residue was taken up in dichloromethane, filtered and chromatographed on silica gel using a gradient of 100% hexane to 80:20 hexane:EtOAc. TLC, staining with KMnO$_4$, and pooling of the product fractions provided the desired product (6.08 g, 50%) as a clear oil. GC/MS calculated for C14H24O5 272, observed 272.

b) 8-oxodecanoic Acid 8-ethyl 1-methyl 2-propionyloctanedioate (3.08 g, 11.31 mmol) was treated with sodium hydroxide (25 ml, 100 mmol) (4 M) and Ethanol (25 ml). This was refluxed for 5 hours and then cooled to room temperature. The reaction was partially concentrated on the rotavap to remove some ethanol. Next, it was transferred to a 250 ml separatory funnel and washed with MTBE (2×75 ml). The aqueous layer was cooled to 0° C. and made acidic (pH~1) using concentrated HCl. Next, the acidified solution was extracted with dichloromethane, dried (Na$_2$SO$_4$), filtered and concentrated providing an off-white solid (1.56 g, 70%). $^1$H NMR (300 MHz, CDCl$_3$, ppm) 1.05 (t, J=7 Hz, 3H), 1.27-1.38 (m, 4H), 1.53-1.68 (m, 4H), 2.32-2.45 (m, 6H); $^{13}$C NMR (75 MHz, CDCl$_3$, ppm) 8.0, 23.8, 24.6, 28.9, 29.0, 34.1, 36.1, 42.4, 180.0, 212.1.

EXAMPLE 8

8-hydroxydecanoic Acid

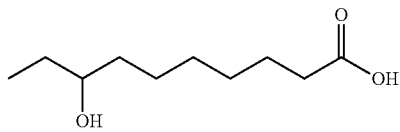

a) methyl 8-oxodecanoate

8-Oxodecanoic acid, from example 5 above, (0.5 g, 2.68 mmol) was added to a 50 ml round bottom flask followed by Methanol (11 ml) and amberlyst 15 (0.43 g, 2.68 mmol). The contents were stirred at room temperature following the reaction by TLC. After 24 hours, the amberlyst was removed by filtration through filter paper and the methanol was evaporated. The product was chromatographed on silica gel using a gradient of 100% hexane to 50:50 hexane:EtOAc. The fractions were TLC'd staining with $KMnO_4$. The product containing fractions were combined aid evaporated providing the desired product (0.36 g, 67%) as a clear oil. GC/MS calculated for $C_{11}H_{20}O_3$ 200, observed 200.

b) methyl 8-hydroxydecanoate

Methyl 8-oxodecanoate (0.3607 g, 1.801 mmol) was dissolved in methanol (10 ml) and cooled to 0° C. Next, sodium borohydride (0.082 g, 2.167 mmol) was added and the reaction was warmed to room temperature for 1 hour. After an hour, the starting material had been consumed based on TLC analysis (70:30 hexane:EtOAc) staining $KMnO_4$. The reaction was cooled to 0° C. and quenched with saturated $NH_4Cl$. A white precipitate formed, which was removed by filtration and washing with MeOH. The filtrate was evaporated, diluted with water and extracted with EtOAc. The EtOAc layer was dried ($Na_2SO_4$), filtered and concentrated providing a clear oil. The product was dissolved in a small amount of DCM and chromatographed on a 40 g $SiO_2$ column using a gradient of 100% hexane to 50:50 hexane:EtOAc. The fractions were analyzed by TLC 70:30 hexane:EtOAc and product containing fractions were combined and concentrated providing methyl 8-hydroxydecanoate (0.24 g, 65%) as a clear oil. $^1$H NMR (300 MHz, $CDCl_3$, ppm) 0.94 (t, J=7 Hz, 3H), 1.33-1.51 (m, 11H), 1.54-1.65 (m, 2H), 2.30 (t, J=7 Hz, 2H), 3.42-3.58 (m, 1H), 3.66 (s, 3H); $^{13}$C NMR (75 MHz, $CDCl_3$, ppm) 10.1, 25.1, 25.7, 29.3, 29.5, 30.4, 34.3, 37.1, 51.6, 73.5, 174.5; GC/MS calculated for $C_{11}H_{22}O_3$ 202, observed ($M-CH_2CH_3$) 173.

c) 8-hydroxydecanoic Acid

Methyl 8-hydroxydecanoate (0.2381 g, 1.177 mmol) was dissolved in THF (5 ml) and methanol (5 ml) and cooled to 0° C. Next, lithium hydroxide (0.706 ml, 1.412 mmol) was added and the reaction was warmed to room temperature. The progress was monitored by TLC (70:30 hexane:EtOAc) staining with $KMnO_4$. After 3 hours, starting material still remained so an additional 0.7 ml of 2M LiOH was added and stirring was continued. After 6 hours, a TLC showed that the starting material had largely been consumed. The reaction was concentrated on the rotavap to remove the methanol and THF. The residue was diluted with 1M KOH (15 ml) and washed with MTBE (2×30 ml). The aqueous layer was cooled to 0° C. and adjusted to pH~1 by dropwise addition of concentrated HCl. The product was extracted using ethyl acetate (2×50 ml). The ethyl acetate layer as dried ($Na_2SO_4$), filtered and concentrated providing a clear oil. The oil was placed on the vacuum pump overnight at 50° C. providing the 9-hydroxydecanoic acid (0.25 g, 86%) as an oil that slowly solidified into a low melting solid. $^1$H NMR (300 MHz, $CDCl_3$, ppm) 0.94 (t, J=7 Hz, 3H), 1.30-1.55 (m, 11H), 1.59-1.67 (m, 2H), 2.35 (t, J=7 Hz, 2H), 3.50-3.55 (m, 1H); $^{13}$C NMR (75 MHz, $CDCl_3$, ppm) 10.1, 24.8, 25.6, 29.2, 29.5, 30.4, 34.0, 37.0, 73.5, 179.1.

EXAMPLE 9

Preparation of Compounds is Low Fat Milk

Low fat milk (1.5-2% fat) was used as a base to evaluate the creamyness/mouthfeel enhancement properties of the compounds. Samples with compound were compared to the base without compound added. Results are shown in Table 1 below.

TABLE 1

Low fat milk evaluation

| Compound | Taste Description | Concentration (ppm) |
| --- | --- | --- |
| 8-Hydroxy decanoic acid | Slight mouthfeel | 4 |
| 9-Hydroxy decanoic acid | Slightly more mouthfeel | 4 |

EXAMPLE 10

Preparation of Compound is Skim Milk

Skim milk was used as a base to evaluate the creamyness/mouthfeel enhancement properties of the compounds. Samples with compound were compared to the base without compound added. Results we shown in Table 2 below.

TABLE 2

Skim milk evaluation

| 8-Hydroxy decanoic acid | Some mouthfeel effect | 10 |
| --- | --- | --- |
| 9-Hydroxy decanoic acid | Some mouthfeel effect | 10 |
| 9-hydroxy gamma decalactone | No mouthfeel | 10 |
| 8-hydroxy gamma decalactone | Some mouthfeel effect | 10 |

EXAMPLE 11

Preparation of Compounds in Sweetened Yogurt

Sweetened yogurt with flavor was used as a base to evaluate the creamyness/mouthfeel enhancement properties of the compounds. The yogurt base was sweetened with 5% sucrose and 0.03% creamy mouthfeel flavor (Givaudan 97584209). Samples with compound were compared to the sweetened base without compound added. The results are shown in Table 3 below:

TABLE 3

Sweetened yogurt evaluation.

| Compound | Taste Description | Concentration (ppm) |
| --- | --- | --- |
| 8-Hydroxy decanoic acid | Lingering waxy profile, fattier. fuller, slightly more creamy than the control, milky, big impact on creaminess, more mouthfeel | 10 |
| 9-Hydroxy decanoic acid | Lingering waxy profile, fattier. fuller profile, creamier, some mouthcoating, very milky, slightly more creamy milk. best mouthfeel, improvement on creaminess | 10 |

EXAMPLE 12

Preparation of Compounds in a Kefir Drink

A commercial Kefir drink was used as a base to evaluate the creamyness/mouthfeel enhancement properties of the compounds. Samples with compound were compared to the base without compound added. Results are shown in Table 4 below.

TABLE 4

Kefir Evaluation

| Compound | Taste Description | Concentration (ppm) |
|---|---|---|
| 8-Hydroxy decanoic acid | Fatty mouthfeel, cleaner dairy, not as sour | 2 |
| 8-Hydroxy decanoic acid | Creamy. fatty mouthfeel. good mouthfeel. not as sour, more milk/dairy-creamlike | 5 |
| 9-Hydroxy decanoic acid | Very creamy, slight mouthfeel, more cultured, slightly cheesier, much creamier | 2 |
| 9-Hydroxy decanoic acid | Very creamy, mouth-coating, smooth, creamy. cultured, slight cream cheese like notes. creamier | 5 |
| 8-hydroxy gamma decalactone | Much creamier, fattier, fuller, creamier backend | 2 |
| 8-hydroxy gamma decalactone | more mid body, creamier | 5 |
| 9-hydroxy gamma decalactone | More creamy than control, upfront fullness. slightly creamier. fattier. dairy like, front to mid seems more creamier | 2 |
| 9-hydroxy gamma decalactone | More dairy note, more mid body. fullness mid profile, slightly creamier | 5 |

EXAMPLE 13

Preparation of Compounds in a Sucralose Base

Compounds were prepared in a sucralose base containing 80 ppm sucralose in water. Compounds were calculated in the base and compared to the base without may compound added. Taste descriptors are listed in the table below.

A solution containing 80 ppm sucralose in water was used as a base to evaluate the bitter masking properties of the compounds. Samples with compound were compared to the base without compound added. Results are shown in Table 5 below.

TABLE 5

Sucralose evaluation

| Compound | Taste Description | Concentration (ppm) |
|---|---|---|
| 9-hydroxy gamma decalactone | Floral, little masking, waxy, slightly musty, better upfront | 2 |
| 9-hydroxy gamma decalactone | Some effect | 5 |
| 9-hydroxy gamma decalactone | High offnote. masks sweetness and bitterness at end, earthy, herby, green. reduces bitterness. masks back end, delayed waxy/mouthcoating effect | 10 |
| 8-hydroxy gamma decalactone | Floral, little masking, waxy, plastic, fatty note. slight upfront masking | 2 |
| 8-hydroxy gamma decalactone | Some effect | 5 |
| 8-hydroxy gamma decalactone | Masks sweetness, floral, herby. green. slight fatty character. mouthcoating, lingering. dairy fatty acid note | 10 |

TABLE 5-continued

Sucralose evaluation

| Compound | Taste Description | Concentration (ppm) |
|---|---|---|
| 9-Hydroxy decanoic acid | Less bitter. lingering, more velvety, sugar-like, more mouthfeel, less lingering, mouthcoating, masking | 2 |
| 9-Hydroxy decanoic acid | Backend masks lingering. very full. creamy sweet dairy. creamier | 5 |
| 9-Hydroxy decanoic acid | Nice mouthfeel, full upfront to mid profile, masks some linger | 10 |
| 8-Hydroxy decanoic acid | Less lingering, more mouthfeel. good masking. slight effect | 2 |
| 8-Hydroxy decanoic acid | Velvety mouthfeel. very full. masking, slight dairy, fatty | 5 |
| 8-Hydroxy decanoic acid | No masking, adds mouthfeel. middle to end profile, delayed waxy fattiness | 10 |

EXAMPLE 14

Preparation of Compounds in a Rebaudioside A Base

A tasting base was prepared with 300 ppm Rebaudioside A in ater. Compounds were added to the base in the concentrations indicated in the table and compared to the base without compound added. Taste descriptors are listed in Table 6 below.

TABLE 6

Rebaudioside A evaluation

| Compound | Taste Description | Concentration (ppm) |
|---|---|---|
| 9-hydroxy gamma decalactone | Slight fatty note at end. earthy, preserve-like | 2 |
| 9-hydroxy gamma decalactone | Not much | 5 |
| 9-hydroxy gamma decalactone | High offnote, changes profile, earthy, green, herby, slight bitter reduction, slightly fruity, back linger reduced | 10 |
| 8-hydroxy gamma decalactone | Masks lots of bitter, less lingering, offnote, slight fatty/coconut note, slight sweet/bitter linger, moldy earthy, preserve like | 2 |
| 8-hydroxy gamma decalactone | Some masking | 5 |
| 8-hydroxy gamma decalactone | High offnote, masks more sweetness than bitterness, completely changes profile, earthy, herby, slight bitter reduction | 10 |
| 9-Hydroxy decanoic acid | Less bitter, lingering, more velvety, sugar-like, more mouthfeel, pleasant, less lingering, mouthcoating, masking, slight effect | 2 |
| 9-Hydroxy decanoic acid | Less bitter, lingernig, waxy, less bitter end | 5 |
| 9-Hydroxy decanoic acid | Offtaste, not much difference | 10 |

TABLE 6-continued

Rebaudioside A evaluation

| Compound | Taste Description | Concentration (ppm) |
|---|---|---|
| 8-Hydroxy decanoic acid | Less bitter, less bitter lingering, more mouthfeel, masking, mouth feel, less bitter | 2 |
| 8-Hydroxy decanoic acid | Less bitter, less bitter lingering, more sugary, better than 2 ppm, mouthwatering, full, dairy sweet, less bitter | 5 |
| 8-Hydroxy decanoic acid | Helps overall especially back end, slightly fuller | 10 |

EXAMPLE 15

Preparation of Compounds in a Red Bull™ Energy Drink

A commercial Red Bull™ Energy drink was used as a base to evaluate the masking properties of the compounds. Compounds were added to the base in the concentrations indicated in the table and compared to the base without compound added. Taste descriptors are listed in Table 7 below.

TABLE 7

Red Bull ™ drink evaluation

| Compound | Taste Description | Concentration (ppm) |
|---|---|---|
| 9-hydroxy gamma decalactone | Less sweetness, strong linger | 5 |
| 9-hydroxy gamma decalactone | Good masking, offnote | 10 |
| 8-hydroxy gamma decalactone | Good masking, less sweet upfront | 5 |
| 8-hydroxy gamma decalactone | Offnote, similar to control | 10 |
| 9-Hydroxy decanoic acid | Masks better than control | 10 |
| 8-Hydroxy decanoic acid | Similar to control | 10 |

Although the embodiments have been described in detail through the above detailed description and the preceding examples, these examples are for the purpose of illustration only and it is understood that variations and modifications can be made by one skilled in the art without departing from the spirit and the scope of the invention. It should be understood that the embodiments described above are not only in the alternative, but can be combined.

We claim:

1. A method of modifying the taste of a consumable, comprising adding to a consumable base at least one compound of the formula I

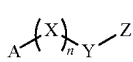

in which
(a) A is the moiety

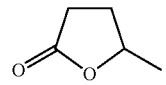

(b) n is from 0-7, such that X is absent or —CH$_2$— resulting in a linear alkylene group in which n is from 1-7; and
(c) Z is absent and Y is a moiety selected from the groups —CHO, or —CH$_2$OH; or
(d) Z is present and is a C$_{1-7}$ linear alkane, and Y is selected from —CHOH or —CO, wherein the compound of formula (I) is added in concentrations of from 0.3-20 ppm, based on the weight of the consumable.

2. The method according to claim 1, in which the modified taste comprises an enhanced mouthfeel or creaminess.

3. The method according to claim 1, in which the consumable base comprises at least one ingredient that is bitter or that contributes to bitterness and the modified taste comprises a reduction of bitterness contributed by said at least one ingredient.

4. A method of modifying the taste of a consumable, comprising adding to a consumable base at least one compound selected from the group consisting of 8-hydroxydecanoic acid and 9-hydroxydecanoic acid, wherein the compound is added in concentrations of from 0.5-25 ppm, based on the weight of the consumable.

5. A consumable composition comprising compound of the formula II,

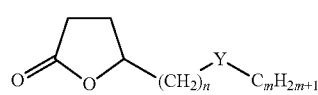

in which the values of n, m and Y are selected according to the following table:

| n | Y | m |
|---|---|---|
| 1 | CO | 2, 3, 5, 6 |
| 1 | CHOH | 2, 3 |
| 3 | CO or CHOH | 1, 2, 3 |
| 4 | CO | 2, 3 |
| 4 | CHOH | 1, 2, 3 |
| 5 | CO | 1, 2 |
| 5 | CHOH | 1 |
| 6 | CO | 1 |

6. A consumable composition comprising 8-hydroxy gamma decalactone.

7. A consumable composition comprising 9-hydroxy gamma decalactone.

8. The method according to claim 4, in which the modified taste comprises an enhanced mouthfeel or creaminess.

9. The method according to claim 4, in which the consumable base comprises at least one ingredient that is bitter or that contributes to bitterness and the modified taste comprises a reduction of bitterness contributed by said at least one ingredient.

* * * * *